United States Patent [19]
Finch et al.

[11] Patent Number: 5,954,201
[45] Date of Patent: *Sep. 21, 1999

[54] INDIVIDUALLY PACKAGED ABSORBENT ARTICLE

[75] Inventors: Valerie Victoria Finch, Neenah; Pamela Jean DeShaney, Readfield; Tammy Jo Balzar, Menasha; Janet Jessie Larsen, Neenah; James Dell Milner, Appleton, all of Wis.

[73] Assignee: Kimberly-Clark Wordwide, Inc., Neenah, Wis.

[ * ] Notice: This patent is subject to a terminal disclaimer.

[21] Appl. No.: 09/057,900

[22] Filed: Apr. 9, 1998

[51] Int. Cl.$^6$ .............................. A16F 13/15; A16B 17/06
[52] U.S. Cl. ...................... 206/440; 206/460; 604/385.1; 604/387
[58] Field of Search .................................... 206/438, 440, 206/441, 363, 460, 813; 604/386, 387, 385.1

[56] References Cited

U.S. PATENT DOCUMENTS

| | | |
|---|---|---|
| 3,561,593 | 2/1971 | Ruda . |
| 3,698,549 | 10/1972 | Glassman . |
| 3,973,567 | 8/1976 | Srinivasan et al. . |
| 4,556,146 | 12/1985 | Swanson et al. . |
| 5,088,993 | 2/1992 | Gaur .......................................... 206/440 |
| 5,181,610 | 1/1993 | Quick et al. . |
| 5,413,568 | 5/1995 | Roach et al. ............................. 206/440 |
| 5,478,336 | 12/1995 | Pigneul .................................... 206/438 |
| 5,484,636 | 1/1996 | Berg, Jr. et al. ......................... 206/440 |
| 5,569,228 | 10/1996 | Byrd et al. ............................... 206/438 |
| 5,569,230 | 10/1996 | Fisher et al. ............................. 206/438 |

FOREIGN PATENT DOCUMENTS 0 750 896 A3  1/1997  European Pat. Off. .
2273279      6/1994  United Kingdom .
WO 97/12572
        A1   4/1997  WIPO .

*Primary Examiner*—Paul T. Sewell
*Assistant Examiner*—Luan K. Bui
*Attorney, Agent, or Firm*—Douglas L. Miller

[57] ABSTRACT

An individually packaged absorbent article, such as a catamenial device, is disclosed. The absorbent article has an outer periphery with first and second ends and first and second longitudinal sides. The absorbent article further has first and second major surfaces, with the second major surface having an garment attachment adhesive secured thereto. The absorbent article is enclosed by a wrapper having first and second ends, first and second longitudinal sides, and first and second major surfaces. The first major surface of the wrapper is releasably affixed to the garment attachment adhesive such that the first and second ends of the wrapper and the first and second longitudinal sides of the wrapper extend beyond the outer periphery of the absorbent article. An attachment device, such as a line of an adhesive or one or more dots of adhesive, is secured to the second major surface of the wrapper and is located closer to the first end than to the second end. The wrapper and the article are folded together as a unit about two fold axes such that the first major surface of the wrapper contacts the attachment device and is releasably secured thereto to form a package. The package has first and second side edges aligned adjacent to the first and second sides of the absorbent article, respectively. Formed approximately at the first and second side edges of the package are first and second seals, respectively. The first and second seals secure the side edges of the package. Located adjacent to and inward of the first and second seals are first and second lines of perforations, respectively. The first and second lines of perforations provide an easy open feature for the package.

23 Claims, 5 Drawing Sheets

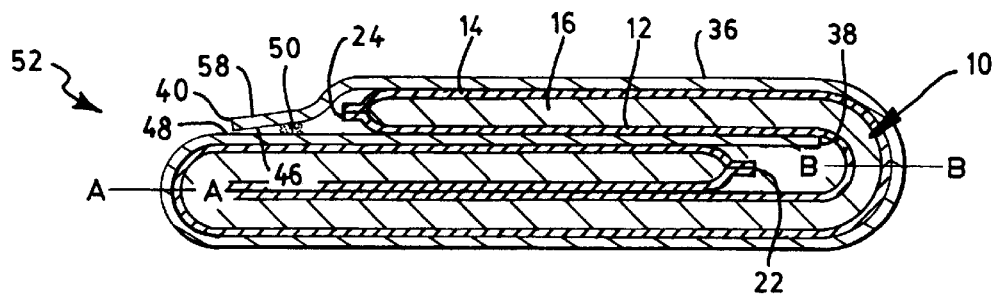
FIG. 8
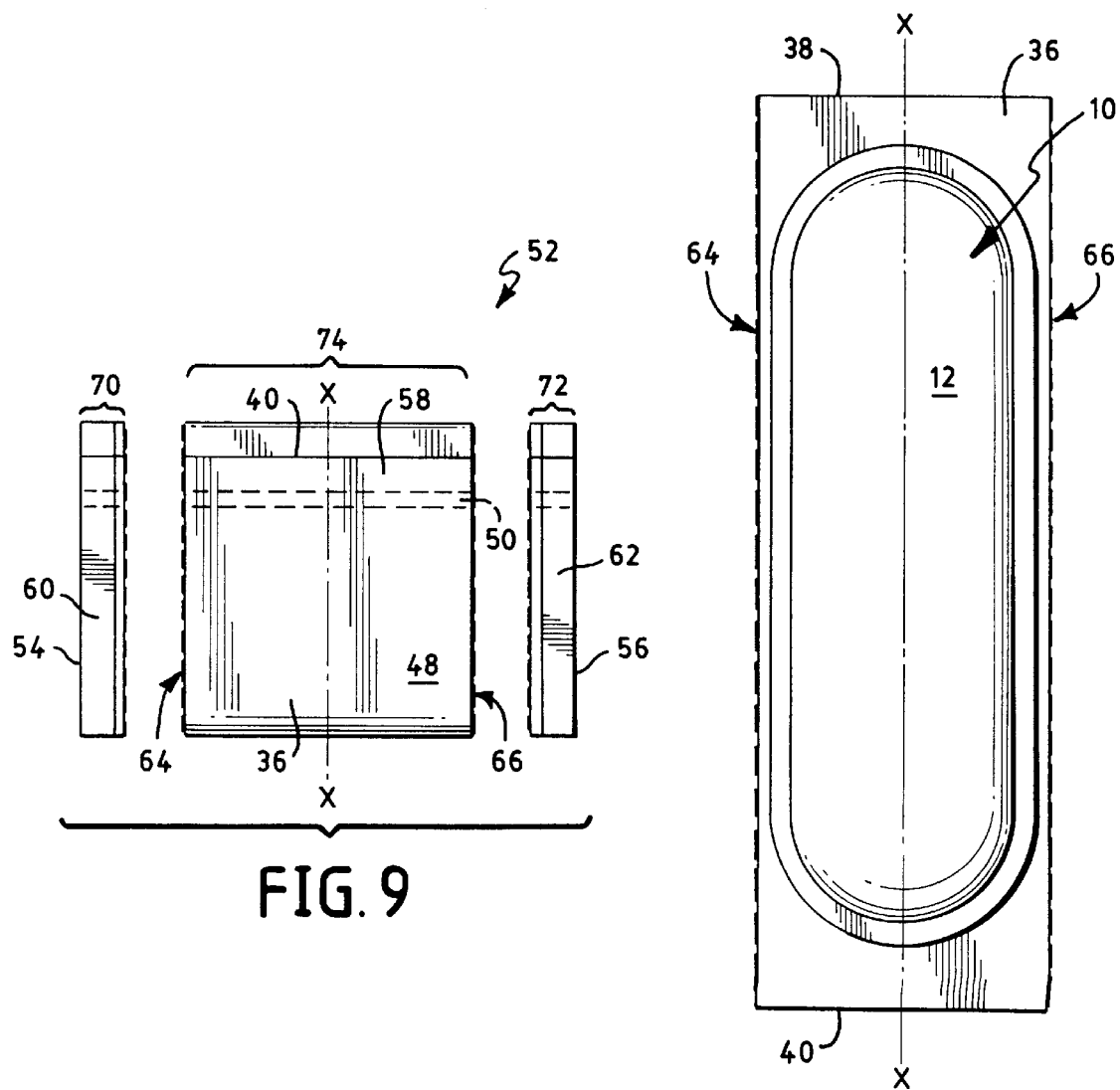
FIG. 9
FIG. 10

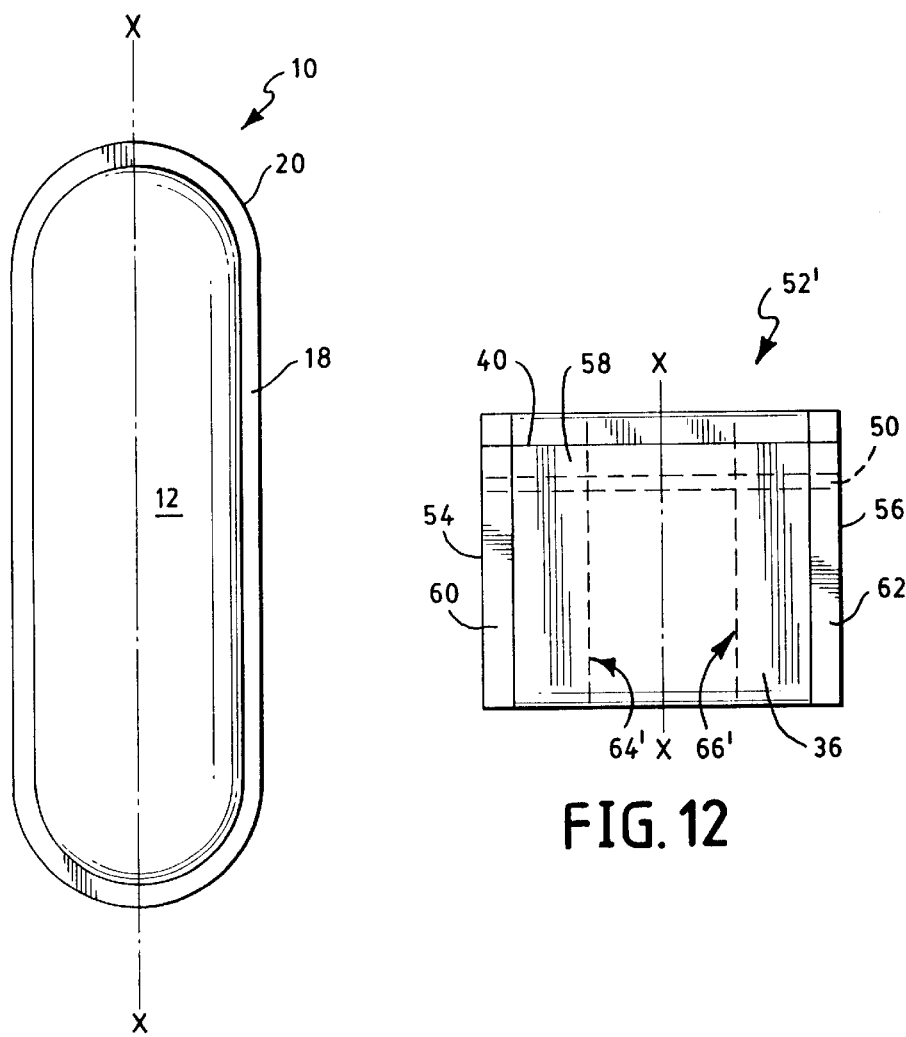
FIG. 12
FIG. 11
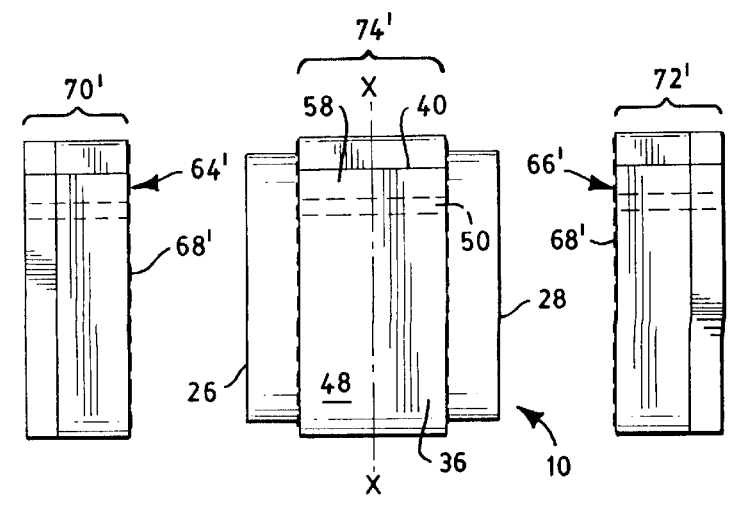
FIG. 13

INDIVIDUALLY PACKAGED ABSORBENT ARTICLE

FIELD OF THE INVENTION

This invention relates to an individually packaged absorbent article, such as a catamenial pad used to absorb menstrual fluid. More specifically, this invention relates to an individually packaged absorbent article wherein the wrapper has two lines of perforations which provide for easy opening.

BACKGROUND OF THE INVENTION

Absorbent articles such as sanitary napkins, panty liners, and other types of catamenial devices are used to absorb menses and other body fluids. Such absorbent articles are primarily disposable and are used during a women's menstrual cycle. In addition, disposable absorbent articles are used between menstrual periods for light incontinence purposes. Since many of these absorbent articles are carried in a woman's purse or pocket prior to use, it is advantageous to individually wrap each article so as to keep it clean. By individually packaging each absorbent article, the manufacturer can be assured that the article will not become contaminated by makeup, perfume, dirt, etc. Because of this, many absorbent articles commercially sold today are individually packaged.

Generally, the wrapper consists of a thin sheet of thermoplastic material, such as polyethylene, which is folded around the absorbent article and is then sealed by the use of heat and/or pressure, by ultrasonics or an adhesive, to form a package. The package is designed to be opened by breaking or tearing the material at or adjacent the seal so as to remove the absorbent article. Normally, the thermoplastic material is designed to tear adjacent to the seal. However, when this occurs, the thermoplastic material acquires a ragged appearance and the tearing operation can be noisy. Most woman desire a package which can be quietly opened to avoid any embarrassing moments. In addition, it has been found that some seals are of a frangible nature such that they will come apart prior to use and therefore allow contamination to enter and contact the absorbent article. This is a detriment in that the consumer expects the absorbent article to be clean in appearance when the package is opened.

Another use for the wrapper is to enclose a soiled sanitary napkin after it has been used by the consumer so that it can be discretely disposed. For this reason, it is advantageous to design a package which can be opened such that a single, large piece of wrapper material remains which can be used to wrap up a soiled sanitary napkin prior to its disposal.

In view of the above, it has been recognized that there is a need for an individually wrapped absorbent article which has an easy open feature and which can be quietly and discreetly opened. It is also advantageous to offer an individually wrapped absorbent article having one or more lines of perforations which enable the wrapper to be cleanly torn apart so that no ragged edges are present.

SUMMARY OF THE INVENTION

Briefly, this invention relates to an individually packaged absorbent article. The absorbent article has an outer periphery with first and second ends and first and second sides. The absorbent article further has first and second major surfaces with the second major surface having a garment attachment adhesive secured thereto. A wrapper having first and second ends, first and second sides, and first and second major surfaces is positioned relative to the absorbent article such that the first surface of the wrapper is releasably affixed to the garment attachment adhesive. In this position, the first and second ends of the wrapper and the first and second sides of the wrapper extend beyond the outer periphery of the absorbent article. The second major surface of the wrapper also contains an attachment device, such as a line of adhesive, which is located closer to the first end than to the second end. The wrapper and the article are folded together about two fold axes such that the first major surface of the wrapper contacts the attachment device and is releasably secured thereto to form a package.

The package has first and second side edges aligned adjacent to the first and second sides of the absorbent article, respectively. A first seal and a second seal are formed approximate the first and second side edges, respectively, of the package for securing the respective side edges together. The wrapper also contains first and second lines of perforations which are formed adjacent to and inward of the first and second seals, respectively. The first and second lines of perforations provide an easy open feature for the package.

The general object of this invention is to provide an individually packaged absorbent article, such as a catamenial pad. A more specific object of this invention is to provide an individually packaged absorbent article which contains a pair of perforation lines which provide an easy opening feature for the package.

Another object of this invention is to provide an individually packaged absorbent article which is easy to assemble and is easy to open.

A further object of this invention is to provide an individually packaged absorbent article which allows the wrapper, after it has been removed from the absorbent article, to be used to discreetly dispose of a soiled sanitary napkin.

Still another object of this invention is to provide an individually packaged absorbent article having first and second spaced apart lines of perforations which can be easily broken in a discreet and quiet manner.

Still further, an object of this invention is to provide an individually packaged sanitary napkin or panty liner which includes a wrapper having first and second lines of perforations which extend along the entire length of the wrapper.

Other objects and advantages of the present invention will become more apparent to those skilled in the art in view of the following description and the accompanying drawings.

BRIEF DESCRIPTION OF THE DRAWINGS

FIG. 8 is a cross-sectional view of the packaged absorbent article shown in FIG. 7 taken along line 8—8.

FIG. 9 is a top view of the package shown in FIG. 7 with the sealed side edges torn off of the central portion of the wrapper which surrounds the absorbent article.

FIG. 10 is a top view of the absorbent article and wrapper after both have been unfolded from the position shown in FIG. 9.

FIG. 11 is a top view of the absorbent article after it has been removed from the wrapper and is ready for use.

FIG. 12 is an alternative embodiment of the package having the first and second lines of perforations spaced apart from the first and second seals.

FIG. 13 is a top view of the package shown in FIG. 12 with the sealed side edges torn off of the central portion of the wrapper which surrounds the absorbent article.

DETAILED DESCRIPTION OF THE PREFERRED EMBODIMENTS

Figure 1:
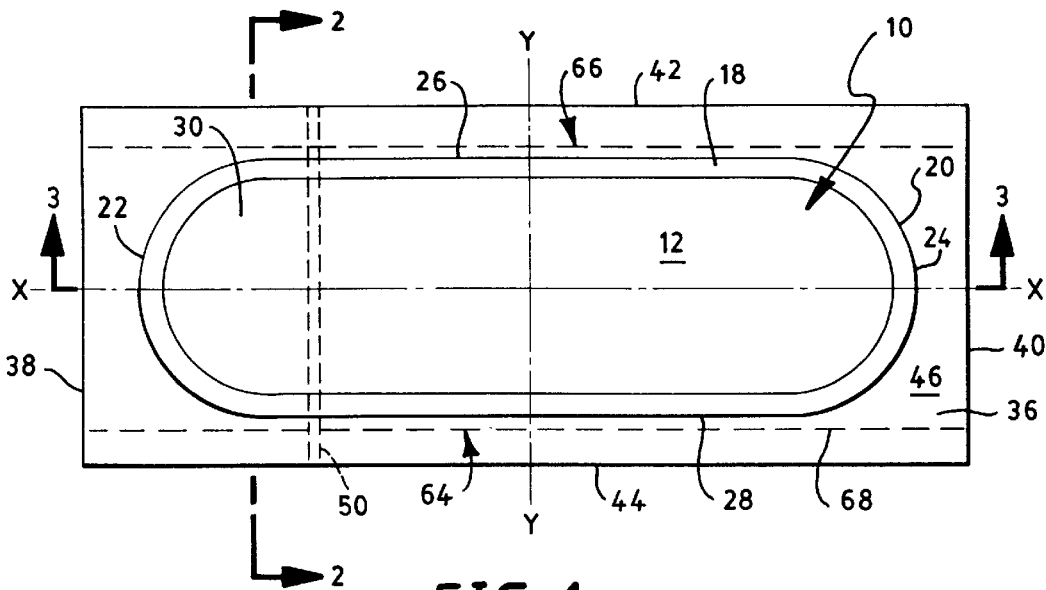
FIG. 1 is a top view of an absorbent article positioned above a rectangular shaped wrapper.
Figure 2:
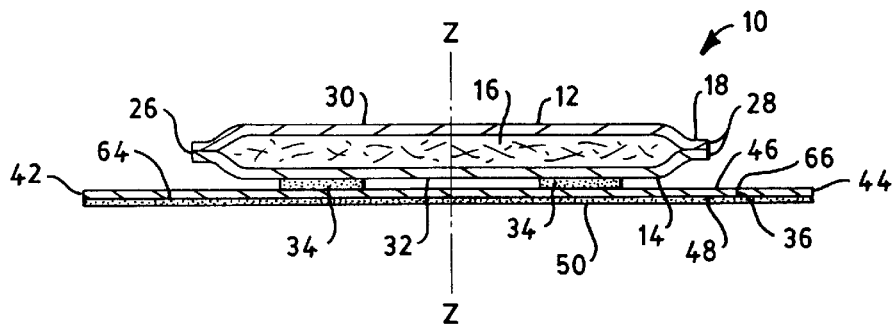
FIG. 2 is a cross-sectional view of the absorbent article and wrapper shown in FIG. 1 taken along line 2—2.
Figure 3:
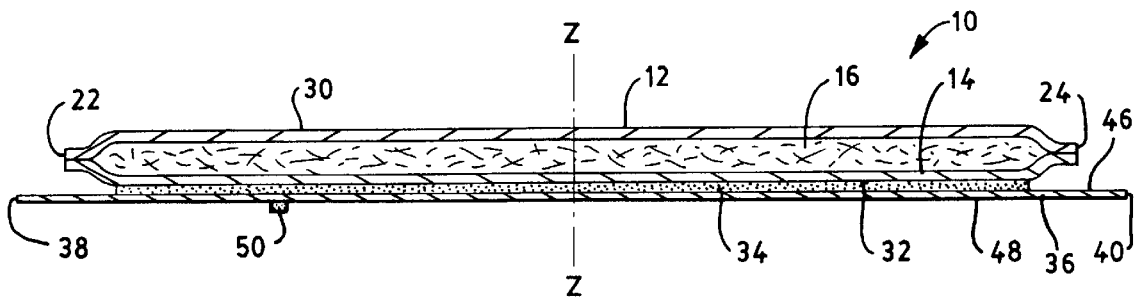
FIG. 3 is a cross-sectional view of the absorbent article and wrapper shown in FIG. 1 taken along line 3—3.

Referring to FIGS. 1, 2 and 3, an absorbent article 10 is shown. The absorbent article 10 can be a catamenial device such as a sanitary napkin, a panty liner, an incontinence pad, or any other type of absorbent article which can be used to absorb menstrual fluid, urine, body fluid, body exudate, etc. For purposes of describing this invention, the absorbent article 10 will be referred to as a sanitary napkin. The absorbent article 10 includes a liquid permeable cover 12, a liquid-impermeable baffle 14 and an absorbent 16. The cover 12 and the baffle 14 cooperate to enclose the absorbent 16. The cover 12 and the baffle 14 can extend beyond the outer periphery of the absorbent 16 to form a peripheral seal 18. The peripheral seal 18 establishes the outer periphery 20 of the absorbent article 10.

The absorbent article 10 is an elongate member having a first end 22 and a second end 24 and a first longitudinal side 26 and a second longitudinal side 28. The first and second ends, 22 and 24 respectively, are spaced apart from one another as are the first and second longitudinal sides, 26 and 28 respectively. The absorbent article 10 has a longitudinal central axis x—x, a transverse central axis y—y and a vertical axis z—z. The absorbent article 10 further contains a first major surface 30 and a second major surface 32. The first major surface 30 is designed to contact the body of the user while the second major surface 32 is spaced away from the body of the user. The second major surface 32 has a garment attachment adhesive 34 secured thereto. The garment attachment adhesive 34 is shown in FIG. 2 as being two separate strips of adhesive which are spaced apart from one another and which have a width of from about 0.25 inches to about 1 inch (about 6.4 mm to about 25 mm). The length of the adhesive strips can vary and may extend over a major portion of the second major surface 32 if desired. Alternatively, the adhesive strips can extend the entire length of the second major surface 32.

The absorbent article 10 is positioned on a wrapper 36 which can be a thin layer of material such as a thermoplastic film made from polypropylene, polyethylene or a laminate of two or more films. The wrapper 36 should be liquid-impermeable and should have a thickness of less than about 5 mils, preferably less than about 3 mils, and more preferably, less than about 2 mils. The wrapper 36 is preferably formed from a polyethylene film having a thickness of less than about 2 mils. The wrapper 36 can be colored and/or contain a pattern. Preferred colors include white, peach and rose. Alternatively, the wrapper 36 can be made of different colors or include multiple colors if desired.

It should be noted that some absorbent articles which are commercially available use a releasable peel strip to cover the garment-facing adhesive. The present invention does not use a releasable peel strip and therefore provides several advantages. First, the absence of a peel strip provides a cost saving to the manufacturer. Second, the user does not have the added step of removing the peel strip prior to securing the absorbent article to her undergarment. A third advantage is that the absence of a peel strip reduces waste.

The wrapper 36 has a first end 38 and a second end 40, a first longitudinal side 42 and a second longitudinal side 44, and a first major surface 46 and a second major surface 48. The first and second ends, 38 and 40 respectively, are spaced apart from one another as are the first and second longitudinal sides, 42 and 44 respectively. The first major surface 46 of the wrapper 36 is releasably affixed to the garment attachment adhesive 34 such that the first and second ends, 38 and 40 respectively, of the wrapper 36 and the first and second sides, 42 and 44 respectively, of the wrapper 36 extend beyond the outer periphery 20 of the absorbent article 10. The first major surface 46 can be coated or treated with silicone or another substance which will allow the adhesive 34 to easily separate therefrom.

An attachment device 50 is secured to the second major surface 48 of the wrapper 36 and is located closer to the first end 38 than to the second end 40. The attachment device 50 can be a spot of adhesive or a line of adhesive which extends transversely across the width of the wrapper 36. Alternatively, the attachment device 50 can be one or more individual dots of adhesive which are separated from one another. The attachment device 50 can also include mechanical fasteners, Velcro fasteners, hook-and-loop fasteners, as well as other types of attachment devices known to those skilled in the art. For purposes of this invention, the attachment device 50 is shown to be a line of adhesive extending across the width of the wrapper 36. The width of the line of adhesive 50 should be less than about 0.5 inches (about 13 mm), preferably less than about 0.25 inches (about 6.4 mm), and most preferably, less than about 0.15 inches (about 4 mm). Although the attachment device 50 is shown to be a continuous line of adhesive which extends transversely across the width of the wrapper 36, it is possible to form the line of adhesive in an intermittent fashion if desired.

Figure 4:
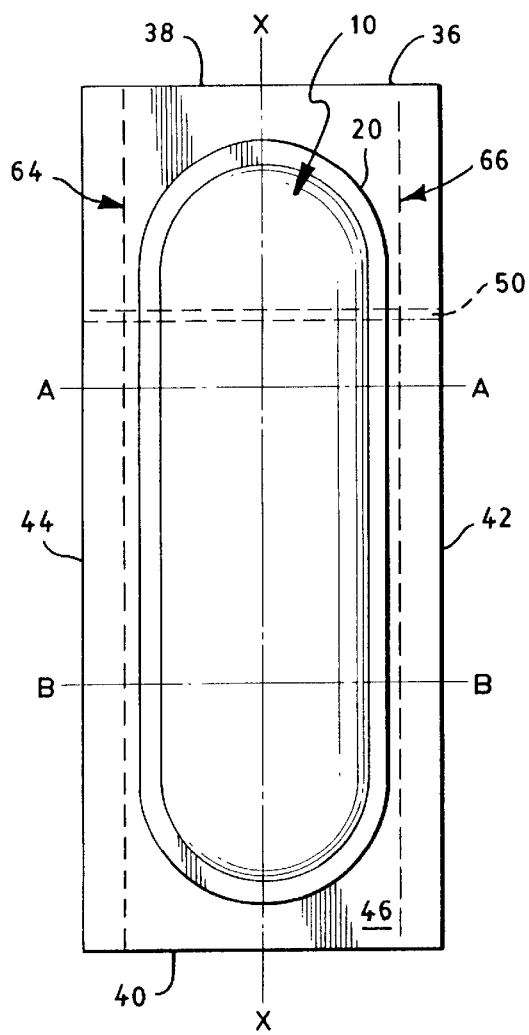
FIG. 4 is a top view of the absorbent article and wrapper showing the location of the two fold lines A—A and B—B.

Referring to FIGS. 4–7, the absorbent article 10 and the wrapper 36 are folded together as a unit about two fold axes or lines designated A—A and B—B. The two fold axes A—A and B—B can be located at equal or different distances from the first and second ends, 38 and 40 respectively, of the wrapper 36 so that when the wrapper 36 and the absorbent article 10 are folded together, the second end 40 will either be flush with or spaced apart from the fold axes A—A. In FIG. 4, the absorbent article 10 is shown positioned on the wrapper 36 such that the first and second ends, 38 and 40 respectively, and the first and second longitudinal sides, 42 and 44 respectively, of the wrapper 36 extend at least about 0.25 inches (about 0.64 mm) beyond the outer periphery 20 of the absorbent article 10. More preferably, the first and second ends, 38 and 40 respectively, and the first and second longitudinal sides, 42 and 44 respectively, of the wrapper 36 extend less than about 0.5 inch (about 13 mm) beyond the outer periphery 20 of the absorbent article 10.

Figure 5:
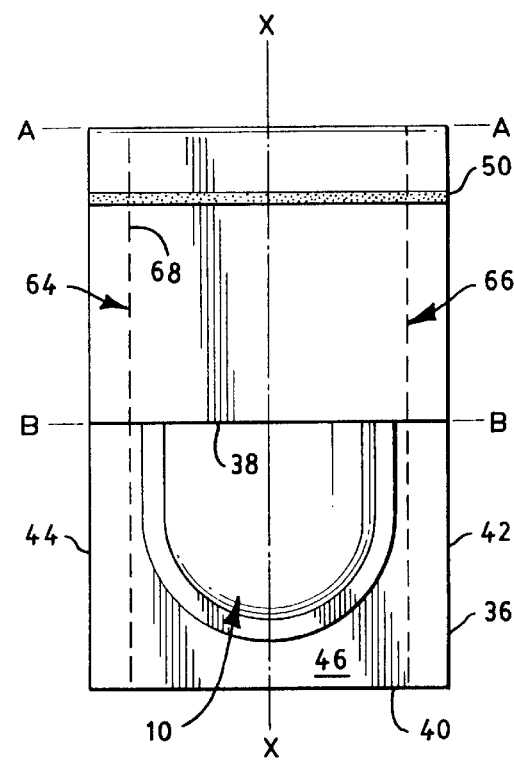
FIG. 5 is a top view of the absorbent article and wrapper having been folded along the first fold line A—A.

The absorbent article 10 and the wrapper 36 are folded along the first fold axis or line A—A to arrive at a configuration as that shown in FIG. 5. As seen in FIG. 5, the attachment device 50 is exposed so that when the remaining portion of the wrapper 36 is folded along the second fold axis B—B, the first major surface 46 of the wrapper 36 will come in contact with the attachment device 50 and be releasably secured thereto. The attachment device 50 is designed such that it will easily release from the first major surface 46 with a small amount of pressure.

Figure 6:
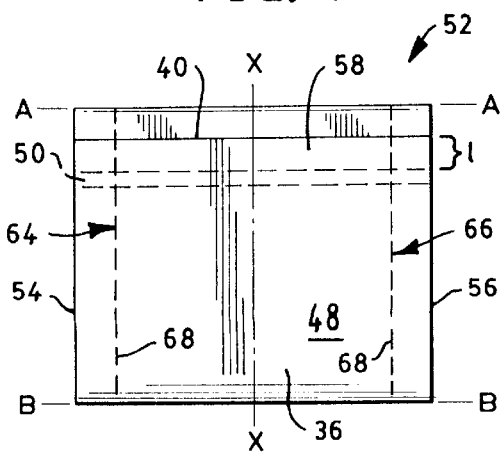
FIG. 6 is a top view of the absorbent article and wrapper having been folded a second time along the fold line B—B such that the first surface of the wrapper contacts the attachment device located on the second surface of the wrapper.

Referring to FIG. 6, the absorbent article 10 and the wrapper 36 are folded along the second fold axis or line B—B to form a package 52. The package 52 has a first side edge 54 and a second side edge 56. The two side edges 54 and 56 can be aligned parallel to one another. Preferably, the first and second side edges, 54 and 56 respectively, are aligned parallel to the first and second sides, 26 and 28 respectively, of the absorbent article 10. The package 52 will also contain a flap 58 which is formed from the wrapper 36. The flap 58 is comprised of material located between the attachment device 50 and the second end 40 of the wrapper 36. This flap 58 can vary in size but preferably has a length L which is less than about 1 inch (about 25 mm), preferably less than about 0.5 inches (about 13 mm), and more preferably, less than about 0.4 inches (about 10 mm). When the individually packaged absorbent article 10 is a sanitary napkin, the length L of the flap 58 is preferably between from about 0.3 inches to about 0.5 inches (about 7 to about 13 mm). The purpose of the flap 58 is to allow the user of the absorbent article 10 to insert one or more tips of her fingers between the flap 58 and the second major surface 48 of the wrapper 36. By inserting one's fingers under the flap 58, the attachment device 50 can be easily broken. For example, the user's index finger and middle finger can be inserted beyond the attachment device 50 and the thumb can be placed on the second major surface 48 of the wrapper 50 such that by pulling outward, the package 52 can be opened.

Figure 7:
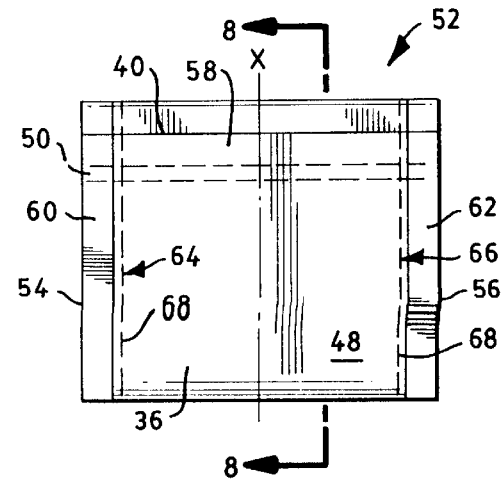
FIG. 7 is a top view of the absorbent article and wrapper folded to form a package having the side edges of the package sealed.
Figure 14:
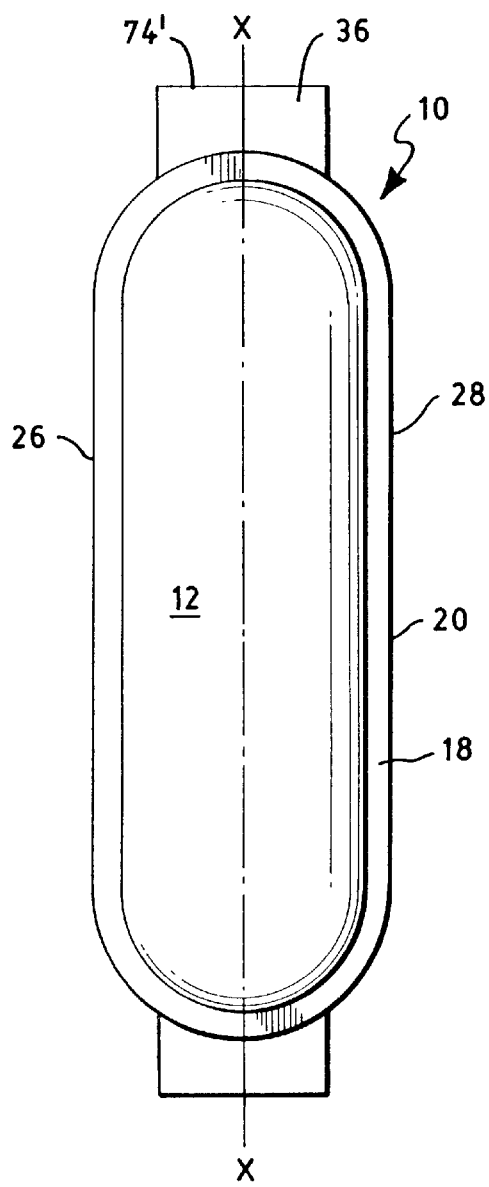
FIG. 14 is a top view of the absorbent article and wrapper after both have been unfolded.

Referring now to FIG. 7, the package 52 is shown having a first seal 60 and a second seal 62. The two seals 60 and 62 are formed approximate or adjacent to the first and second side edges, 54 and 56 respectively of the package 52. The first and second seals, 60 and 62 respectively, function to secure each of the side edges, 54 and 56 respectively, together. Each of the first and second seals, 60 and 62 respectively, can be formed by using heat, pressure, heat and pressure, an adhesive, an ultrasonic bond, or by other types of attachments known to those skilled in the art.

The first and second seals, 60 and 62 respectively, should have a width of less than about 1 inch (about 25 mm), preferably less than about 0.5 inches (about 13 mm), and most preferably, less than about 0.25 inches (about 6.4 mm). When the absorbent article 10 is a sanitary napkin, it has been found that each of the first and second seals, 60 and 62 respectively, should have a width of from between about 1 mm to about 10 mm, and more preferably, a width of from between about 2 mm to about 7 mm.

It should be noted that the first and second seals, 60 and 62 respectively, can be made to be permanent seals. By a "permanent seal" it is meant that the material adjacent to the seal will tear, fracture or break before the seal separates. Alternatively, the first and second seals, 60 and 62 respectively, can be frangible seals. By a "frangible seal" it is meant that the seal will separate before the material adjacent to the seal is actually torn, fractured or separated. For purposes of this invention, it is anticipated that the first and second seals, 60 and 62 respectively, will be of the permanent type. That is, the package 52 will be opened not by breaking the first and second seals, 60 and 62 respectively, but by a different feature which will be explained shortly.

The package 52 also includes a first line of perforations 64 and a second line of perforations 66. The first and second lines of perforations, 64 and 66 respectively, are formed in the wrapper 36 adjacent to the first and second seals, 60 and 62 respectively. The first and second lines of perforations, 64 and 66 respectively, provide an easy open feature for the package 52. The first and second lines of perforations, 64 and 66 respectively, can be linear or nonlinear in configuration. When the first and second lines of perforations 64 and 66, respectively, are linear, they can be aligned adjacent to the first and second side edges, 54 and 56 respectively, of the wrapper 36. By the phrase "adjacent to" it is meant that each of the lines of perforations 64 and 66 are spaced within about 1 inch (about 25 mm), preferably within about 0.5 inches (about 13 mm), and more preferably, within about 0.25 inches (about 6.4 mm) of each of the first and second side edges, 54 and 56 respectively. The first and second lines of perforations, 64 and 66 respectively, are preferably aligned approximately parallel to each of the first and second side edges, 54 and 56 respectively, of the package 52. In addition, the first and second lines of perforations, 64 and 66 respectively, are preferably aligned approximately parallel to the first and second sides, 26 and 28 respectively, of the absorbent article 10. When the absorbent article 10 is a sanitary napkin, having an overall width of from between about 3 inches to about 4 inches (about 76 mm to about 101 mm), the first and second lines of perforations, 64 and 66 respectively, should be spaced a distance of less than about 5 inches (about 127 mm) apart. Preferably, the first and second lines of perforations, 64 and 66 respectively, will be spaced apart a distance of from between about 1 inch to about 4 inches (about 25 mm to about 76 mm). This means that the width of the wrapper 36 will be slightly larger than about 5 inches (about 127 mm) and, more preferably, the width of the wrapper 36 will be slightly larger than about 4 inches (about 101 mm).

Each of the first and second lines of perforations, 64 and 66 respectively, are made up of a plurality of slits 68 which can be arranged in a continuous or intermittent fashion along each of the line of perforations 64 and 66. Preferably, each of the first and second lines of perforations, 64 and 66 respectively, extends the entire length of the wrapper 36. However, if one wishes to limit one or both of the first and second lines of perforations, 64 and 66 respectively, such that they do not extend the entire length of the wrapper 36, this is also possible. Each of the first and second lines of perforation, 64 and 66 respectively, comprise a series of slits 68. Each slit 68 has a length of less than about 0.001 inches (about 0.02 mm), preferably less than about 0.0005 inches (about 0.01 mm) and more preferably, less than about 0.0001 inches (about 0.002 mm). The width of each of the slits 68 can also vary and should roughly be about ¼ of the length of the slit, more preferably, less than about ⅛ of the length of the slit. The slits 68 should extend through the entire thickness of the wrapper 36 but could be formed to only partially extend into the thickness of the wrapper 36, if desired. Each of the slits 68 do not have to be of the same length and/or width nor be of similar configuration if one does not desire to make them so. However, for purposes of manufacturing, it is advantageous to form the slits 68 with a notched wheel or blade such that each of the slits 68 has a similar configuration and has the same dimensions.

The plurality of slits 68 which make up the first and second lines of perforations, 64 and 66 respectively, can be spaced an equal distance apart from one another, or they can be arranged such that several are spaced an equal distance apart and then an extra large land area is present before the next adjacent slit. Alternatively, the slits 68 can be equally spaced apart throughout the entire length of each of the lines of perforations 64 and 66. It should be noted that for best results, the first and second lines of perforations, 64 and 66 respectively, should be identical in configuration, so that the force needed to tear or break apart the material at the first and second lines of perforations, 64 and 66 respectively, will be equal or approximately equal.

Referring now to FIG. 8, a cross-section of the folded absorbent article 10 and wrapper 36 are shown, clearly indicating that the attachment device 50 secures the first major surface 46 of the wrapper 36 to the second major surface 48 of the wrapper 36.

The flap 58 is positioned so as to allows the user's finger(s) to be inserted thereunder and thereby break the attachment device 50 and provide one method of opening the package 52.

The package 52 can be opened in other ways as well. A second way of opening the package 52 is depicted in FIGS. 9–11 wherein the user holds one corner of the package 52 with her left hand, between her index finger and her thumb, and holds the central portion of the package 52 in her right hand. By pulling outward on the material with her left hand, a strip 70 is detached from the main body of the wrapper 36. The consumer can then hold the opposite corner in her right hand and hold the central portion in her left hand and she can tear and remove a second strip 72 by pulling outward with her right hand. This action will leave a wide central strip 74 which encloses the absorbent article 10. The width of the strips 70 and 72 can be relatively narrow, for example, they can be less than about 0.5 inches (about 13 mm), and more preferably, less than about 0.25 inches (about 6.4 mm). With the strips 70 and 72 removed, the user can then grasp the flap 58 between one or more fingers and her thumb, preferably between her index finger and her thumb, and pull the wrapper 36 apart such that it releases from the attachment device 50. The absorbent article 10 and the wrapper 36 can then be opened to the configuration shown in FIG. 10. The absorbent article 10 is then removed from the wrapper 36, as is shown in FIG. 11, and is ready for use. The wrapper 36 is releasably removed and separated from the garment attachment adhesive 34 because the wrapper 36 is made out of a material such as a thermoplastic film, which will not stick to the garment attachment adhesive 34. Alternatively, the wrapper 36 can be treated with a substance, such as a silicone coating, so as to facilitate the easy separation between the wrapper 36 and the garment attachment adhesive 34.

Referring again to FIGS. 8 and 9, another way of opening the package 52 is for the user to hold one corner of the package 52 and insert one or more of her fingers of her other hand under the flap 58 with her thumb positioned against the second major surface 48 of the wrapper 36. By pulling the flap 58 outward away from the package 52, a force will be exerted on the first and second lines of perforations, 64 and 66 respectively, causing them to tear apart thereby unfolding half of the package 52. The user then grasps the first end of the package 52 and pulls upward away from the absorbent article 10. A force will be exerted in the remaining first and second lines of perforations, 64 and 66 respectively, causing them to tear apart. In so doing, one will end up with the strips 70 and 72 remaining attached to the center strip 74. The strips 70 and 72 will be equal in length to the overall length of the wrapper 36. This action will expose the absorbent article 10 which can then be attached to the inner crotch portion of an undergarment.

Referring to FIGS. 12–15, a second alternative embodiment for a package 52' is depicted. In this embodiment, the first and second lines of perforations, 64' and 66' respectively, are spaced a greater distance away from the first and second seals, 60 and 62 respectively, than were shown in FIG. 7. If the absorbent article 10 has a width of from between about 2 inches to about 4 inches (about 50 to about 101 mm) and the wrapper 36 has a width, measured transversely between the first side edge 54 and the second side edge 56, of from between about 3.5 inches to about 5 inches (about 89 mm to about 127 mm), then the first and second lines of perforations, 64' and 66' respectively, will be located at least about 1 inch (about 25 mm) away from the first and second seals, 60 and 62 respectively.

Figure 15:
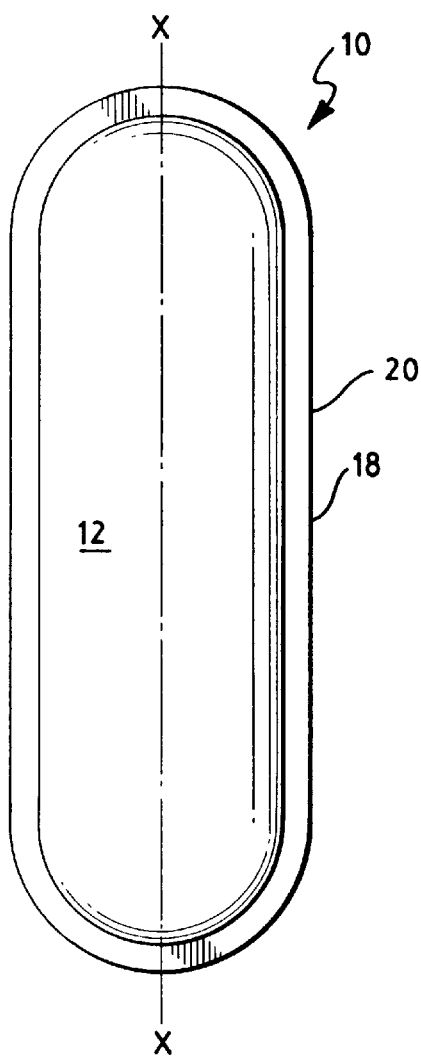
FIG. 15 is a top view of the absorbent article after it has been separated from the wrapper and is ready for use.

Referring to FIG. 13, one will see that the package 52' can be opened in a similar fashion as that shown for package 52, except that when comparing FIG. 15 to FIG. 9, one will notice that the strips 70' and 72' are much wider than the strips 70 and 72. Because of this, the central strip 74' will have a width which is less than the width of the absorbent article 10. This means that as the strips 70' and 72' are broken away from the central strip 74', the first and second longitudinal sides 26 and 28 of the absorbent article 10 will be exposed beyond the width of the central strip 74'. As the absorbent article 10 and the wrapper 36 are unfolded into the configuration shown in FIG. 14, one will notice that the first and second sides, 26 and 28 respectively, of the absorbent article 10, will extend beyond the edges of the central portion 74' of the wrapper 36. The absorbent article 10 can then be removed from the central strip 74' and will be ready to be attached to the inner crotch portion of an undergarment. The absorbent article 10 without the central strip 74' is shown in FIG. 15.

It should be noted that the package 52' can also be opened in the ways discussed above for package 52. The package 52' can also be opened by the user holding one corner of the package 52' and then grasping the flap 58 with her fingers and thumb and pulling upwards away from the remainder of the package 52'. This action will cause the first and second lines of perforations, 64' and 66' respectively, to separate. As the wrapper material between the plurality of slits 68' separates, the first and second lines of perforations, 64' and 66' respectively, will tear along the length of the entire wrapper 36. As noted in reference to the package 52, the first and second lines of perforations, 64' and 66' respectively, can be comprised of a series of slits 68' which can vary in width and length and/or spacing and configuration. The plurality of slits 68' which make up each of the first and second lines of perforations, 64' and 66' respectively, can be spaced an equal distance apart or they can be randomly oriented as the manufacturer desires. However, for best results, it has been found that the plurality of slits 68' should be equally spaced apart from adjacent slits and be formed continuously along the length of the wrapper 36. It is also advantageous to form the slits 68', which make up the first line of perforations 64, the same as the slits 68' which make up the second line of perforations 66'. This will assure that an equal or approximately equal force is required to tear apart both of the first and second lines of perforations, 64' and 66' respectively.

While the invention has been described in conjunction with two specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An individually packaged absorbent article comprising:

a) an absorbent article having an outer periphery with first and second ends and first and second sides, said absorbent article further having first and second major surfaces with said second major surface having a garment attachment adhesive secured thereto;

b) a wrapper having first and second ends, first and second sides and first and second major surfaces, said first major surface of said wrapper being releasably affixed to said garment attachment adhesive such that said first and second ends of said wrapper and said first and second sides of said wrapper extend beyond said outer periphery of said absorbent article;

c) an attachment device secured to said second major surface of said wrapper and located closer to said first end than said second end, said wrapper and said absorbent article being folded together about two fold axes such that said first major surface of said wrapper contacts said attachment device and is releasable secured thereto to form a package, said package having first and second side edges aligned adjacent to said first and second sides of said absorbent article, respectively;

d) a first seal and a second seal formed approximate said first and second side edges, respectively, said first and second seals securing said side edges of said package; and e) first and second lines of perforations formed in said wrapper adjacent to said first and second seals, respectively, said first and second lines of perforations providing an easy open feature for said package.

2. The individually packaged absorbent article of claim 1 wherein said wrapper is polypropylene.

3. The individually packaged absorbent article of claim 1 wherein said wrapper is polyethylene.

4. The individually packaged absorbent article of claim 1 wherein said attachment device is an adhesive.

5. The individually packaged absorbent article of claim 1 wherein said attachment device is a line of adhesive.

6. The individually packaged absorbent article of claim 1 wherein each of said first and second seals is formed by heat and pressure.

7. The individually packaged absorbent article of claim 1 wherein each of said first and second seals is formed by an ultrasonic bond.

8. The individually packaged absorbent article of claim 1 wherein each of said first and second seals has a width of less than about 25 millimeters.

9. The individually packaged absorbent article of claim 8 wherein each of said first and second seals has a width of less than about 10 millimeters.

10. The individually packaged absorbent article of claim 9 wherein each of said first and second seals has a width of less than about 5 millimeters.

11. An individually packaged absorbent article comprising:

a) an absorbent article having an outer periphery with first and second ends and first and second sides, said absorbent article further having first and second major surfaces with said second major surface having a garment attachment adhesive secured thereto;

b) a wrapper having first and second ends, first and second sides and first and second major surfaces, said first major surface of said wrapper being releasably affixed to said garment attachment adhesive such that said first and second ends of said wrapper and said first and second sides of said wrapper extend beyond said outer periphery of said absorbent article;

c) a line of adhesive secured to said second major surface of said wrapper and located closer to said first end than said second end, said wrapper and said absorbent article being folded together about two fold axes such that said second end of said wrapper contacts said line of adhesive and is releasable secured thereto to form a package, said package having first and second side edges aligned approximately parallel to said first and second sides of said absorbent article, respectively;

d) a first seal and a second seal securing said first and second side edges, respectively, of said package together; and e) first and second lines of perforations formed in said wrapper adjacent to said first and second seals, respectively, said lines of perforations providing an easy open feature for said package.

12. The individually packaged absorbent article of claim 11 wherein each of said first and second seals has a width of from between about 1 millimeters to about 10 millimeters.

13. The individually packaged absorbent article of claim 12 wherein each of said first and second seals has a width of from between about 2 millimeters to about 7 millimeters.

14. The individually packaged absorbent article of claim 11 wherein said first and second lines of perforations are spaced apart a distance of less than about 5 inches.

15. The individually packaged absorbent article of claim 14 wherein said first and second lines of perforations are spaced apart a distance of from between about 1 inch to about 4 inches.

16. The individually packaged absorbent article of claim 11 wherein each of said first and second lines of perforations is comprised of a series of slits each having a length of less than about 0.001 inches.

17. An individually packaged absorbent article comprising:

a) an absorbent article having an outer periphery and first and second ends and first and second sides, said absorbent article further having first and second major surfaces with said second major surface having a garment attachment adhesive secured thereto;

b) a wrapper having first and second ends, first and second sides and first and second major surfaces, said first major surface of said wrapper being releasably affixed to said garment attachment adhesive such that said first and second ends of said wrapper and said first and second sides of said wrapper extend beyond said outer periphery of said absorbent article;

c) an adhesive secured to said second major surface of said wrapper and located closer to said first end than said second end, said wrapper and said absorbent article being folded together about two fold axes such that said second end of said wrapper contacts said adhesive and is releasable secured thereto to form a package, said package having first and second side edges aligned adjacent to said first and second sides of said absorbent article, respectively;

d) a first seal and a second seal formed approximate said first and second side edges, respectively, of said package, said first and second seals securing said side edges of said package; and e) first and second lines of perforations formed in said wrapper adjacent to said first and second seals, respectively, said first and second lines of perforations providing an easy open feature for said package.

18. The individually packaged absorbent article of claim 17 wherein each of said first and second lines of perforations is comprised of a series of slits each having a length of less than about 0.001 inches.

19. The individually packaged absorbent article of claim 17 wherein each of said first and second ends and each of said first and second sides of said wrapper extend at least about 0.25 inches beyond said outer periphery of said absorbent article.

20. The individually packaged absorbent article of claim 17 wherein each of said first and second ends and each of said first and second sides of said wrapper extend less than about 0.5 inches beyond said outer periphery of said absorbent article.

21. The individually packaged absorbent article of claim 17 wherein each of said first and second seals has a width of from between about 1 millimeters to about 10 millimeters.

22. The individually packaged absorbent article of claim 17 wherein each of said first and second seals is a permanent seal.

23. The individually packaged absorbent article of claim 17 wherein each of said first and second seals is a frangible seal.

* * * * *